(12) United States Patent
Ho et al.

(10) Patent No.: US 10,276,031 B1
(45) Date of Patent: Apr. 30, 2019

(54) METHODS AND SYSTEMS FOR EVALUATING COMPLIANCE OF COMMUNICATION OF A DISPATCHER

(71) Applicant: MOTOROLA SOLUTIONS, INC., Chicago, IL (US)

(72) Inventors: Shyan Jenq Ho, Penang (MY); V. C. Prakash Vk Chacko, Penang (MY); Kai Boon Khoo, Penang (MY); Mohd Hisham Muddin Che At, Kedah (MY); Wei Ling Cecilia Liaw, Penang (MY)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 0 days.

(21) Appl. No.: 15/836,397

(22) Filed: Dec. 8, 2017

(51) Int. Cl.
*H04W 4/14* (2009.01)
*G08B 25/00* (2006.01)
(Continued)

(52) U.S. Cl.
CPC ....... *G08B 25/006* (2013.01); *G08B 21/0423* (2013.01); *G08B 21/182* (2013.01); *G10L 25/63* (2013.01)

(58) Field of Classification Search
CPC .... G06N 5/022; G06F 17/5009; G07C 5/008; G08B 25/006; G08B 21/0423;
(Continued)

(56) References Cited

U.S. PATENT DOCUMENTS 7,579,541 B2    8/2009 Guldi
8,817,952 B2 *  8/2014 Bentley ............... H04M 3/5116
                                                           379/45
(Continued)

FOREIGN PATENT DOCUMENTS

EP    2937860    10/2015
RU    2233042     7/2004

OTHER PUBLICATIONS

Apple Inc., "iTunes Preview Autoflip—Sheet Music Viewer," website (2017) 3 pages, https://itunes.apple.com/us/app/autoflip-sheet-music-viewer/id413455877?mt=8.
(Continued)

*Primary Examiner* — An T Nguyen
(74) *Attorney, Agent, or Firm* — Michael Best & Friedrich LLP

(57) ABSTRACT

Methods and systems for evaluating compliance of communication of a dispatcher. One system includes an electronic computing device that includes an input device, a transceiver, and one or more electronic processors. The one or more electronic processors are configured to monitor communication between a dispatcher and a caller during a call and determine a type of call. The one or more electronic processors are further configured to determine a conversational procedure based on the type of call and compare a characteristic of the monitored communication to a constraint of the conversational procedure. The one or more electronic processors are further configured to determine that the characteristic of the monitored communication is outside the constraint of the conversational procedure and take an action as a function of determining that the characteristic of the monitored communication is outside the constraint of the conversational procedure.

18 Claims, 5 Drawing Sheets

(51) Int. Cl.
*G10L 25/63* (2013.01)
*G08B 21/04* (2006.01)
*G08B 21/18* (2006.01)

(58) Field of Classification Search
CPC ..... G08B 21/182; G08B 29/188; G01L 25/63; H04M 3/5116; H04L 67/12; H04W 4/028
See application file for complete search history.

(56) References Cited

U.S. PATENT DOCUMENTS

| | | | |
|---|---|---|---|
| 8,873,719 B2 | 10/2014 | Clawson | |
| 9,031,222 B2 | 5/2015 | Wolfeld et al. | |
| 9,491,605 B2* | 11/2016 | Clawson | H04W 4/90 |
| 9,756,495 B1* | 9/2017 | Powers | H04W 4/90 |
| 2005/0085257 A1* | 4/2005 | Laird | A61B 5/04 |
| | | | 455/550.1 |
| 2006/0053010 A1* | 3/2006 | Chapman | H04M 3/2281 |
| | | | 704/235 |
| 2007/0116189 A1 | 5/2007 | Clawson | |
| 2007/0124135 A1* | 5/2007 | Schultz | G10L 17/26 |
| | | | 704/201 |
| 2007/0201664 A1* | 8/2007 | Salafia | H04M 3/5116 |
| | | | 379/201.01 |
| 2010/0286490 A1* | 11/2010 | Koverzin | G06F 19/3418 |
| | | | 600/301 |
| 2012/0207286 A1* | 8/2012 | Clawson | H04M 3/493 |
| | | | 379/45 |
| 2014/0169534 A1* | 6/2014 | Bentley | H04M 3/5116 |
| | | | 379/45 |
| 2014/0211927 A1* | 7/2014 | Clawson | H04M 3/5116 |
| | | | 379/45 |
| 2014/0226532 A1 | 8/2014 | Abbate | |
| 2014/0266690 A1* | 9/2014 | McKinley | G08B 25/006 |
| | | | 340/539.11 |
| 2014/0314212 A1* | 10/2014 | Bentley | H04M 3/5116 |
| | | | 379/38 |
| 2016/0140299 A1* | 5/2016 | Al Harbi | G16H 40/20 |
| | | | 705/2 |
| 2016/0212605 A1* | 7/2016 | Clawson | H04W 4/90 |
| 2017/0161614 A1* | 6/2017 | Mehta | G06N 5/022 |
| 2017/0295477 A1* | 10/2017 | Clawson | H04W 4/90 |
| 2017/0295481 A1* | 10/2017 | Pospiel | H04W 4/90 |
| 2018/0053401 A1* | 2/2018 | Martin | H04L 67/04 |
| 2018/0288224 A1* | 10/2018 | Dizengof | H04M 3/5116 |
| 2018/0301017 A1* | 10/2018 | Dizengof | G08B 25/006 |

OTHER PUBLICATIONS

YouTube, "Dispatcher Tasks—Point of View of a 911 Dispatcher," website (published on Jun. 24, 2015) 1 page, https://www.youtube.com/watch?v=497uMOa8oq0.

PCT/US2018/061787 International Search Report and Written Opinion of the International Searching Authority dated Mar. 6, 2016 (24 pages).

* cited by examiner

METHODS AND SYSTEMS FOR EVALUATING COMPLIANCE OF COMMUNICATION OF A DISPATCHER

BACKGROUND OF THE INVENTION

Dispatchers (for example, public safety dispatchers) receive calls, evaluate an incident that is being described by a caller, and formulate a proper response to attempt to help a caller with the incident. In attempting to help the caller, often times dispatchers use scripts that provide a list of questions and information to be provided to the caller for predetermined incidents (for example, an incident in which a caller needs to perform cardiopulmonary resuscitation (CPR)). Additionally, often times dispatchers communicate with a third party (for example, a first responder) to have the third party travel to the location of the incident to assist the caller with the incident. For example, the dispatcher may communicate with an emergency medical services agency to inform paramedics that an ambulance is needed at a location where a person had a heart attack. To receive calls and communicate with third parties, dispatchers use various devices including, for example, tablets, laptops, desktop computers, phones (for example, cellular or satellite), and devices with interactive displays.

Many such devices further comprise, or provide access to, electronic digital assistants (or sometimes referenced as "virtual partners") that may provide the user thereof with valuable information in an automated (for example, without further user input) or semi-automated (for example, with some further user input) fashion. The valuable information provided to the user may be based on explicit requests for such information posed by the user via an input (for example, such as a parsed natural language input or an electronic touch interface manipulation associated with an explicit request) in which the electronic digital assistant may reactively provide such requested valuable information, or may be based on some other set of one or more context or triggers in which the electronic digital assistant may proactively provide such valuable information to the user absent any explicit request from the user.

As some existing examples, electronic digital assistants such as Siri provided by Apple, Inc.® and Google Now provided by Google, Inc.®, are software applications running on underlying electronic hardware that are capable of understanding natural language, and may complete electronic tasks in response to user voice inputs, among other additional or alternative types of inputs. These electronic digital assistants may perform such tasks as taking and storing voice dictation for future reference and retrieval, reading a received text message or an e-mail message aloud, generating a text message or e-mail message reply, looking up requested phone numbers and initiating a phone call to a requested contact, generating calendar appointments and providing appointment reminders, warning users of nearby dangers such as traffic accidents or environmental hazards, and providing many other types of information in a reactive or proactive manner.

BRIEF DESCRIPTION OF THE SEVERAL VIEWS OF THE DRAWINGS

The accompanying figures, where like reference numerals refer to identical or functionally similar elements throughout the separate views, which together with the detailed description below are incorporated in and form part of the specification and serve to further illustrate various embodiments of concepts that include the claimed invention, and to explain various principles and advantages of those embodiments.

Figure 1A:
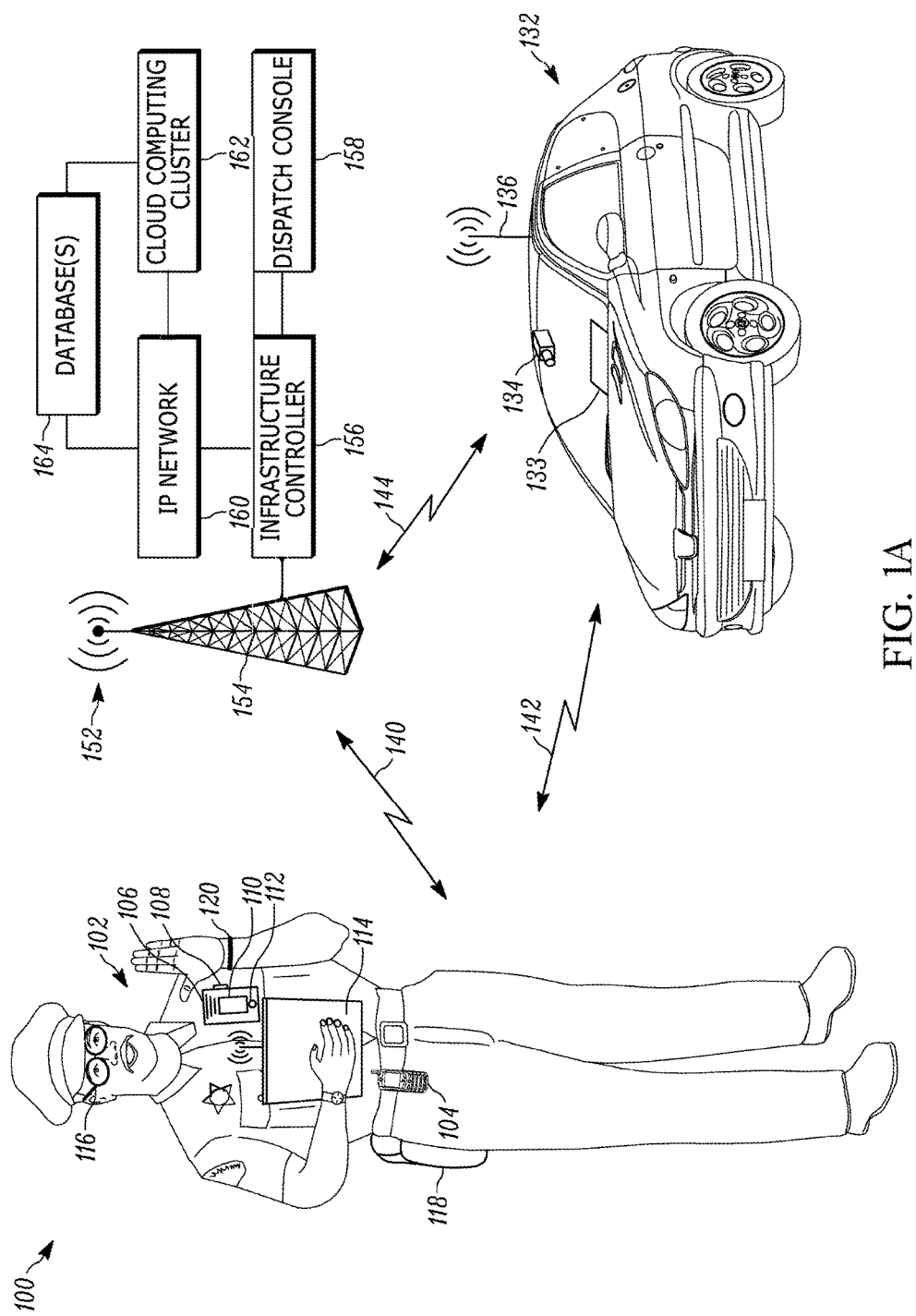
FIGS. 1A and 1B are system diagrams illustrating a system for operating an electronic digital assistant, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

Dispatchers (for example, public safety dispatchers) receive calls relating to incidents of various degrees of severity. For example, a call relating to a cat stuck in a tree may be considered to have a low severity level while a call relating to a person having heart attack may be considered to have a high severity level. Depending on the severity level of the incident, the speed at which information from the call is relayed to a third party (for example, a first responder) may be important. With reference to the above examples, it may be more important to immediately dispatch paramedics to the location of the person having the heart attack than to immediately dispatch a firefighter to the location of the cat stuck in the tree.

Additionally, as noted above, dispatchers often use scripts that provide a list of questions and information to be provided to the caller for predetermined incidents. When dispatchers deviate from the script or proceed through the script too slowly, it may be indicative that the caller does not understand the information that the dispatcher is attempting to convey or that the dispatcher is not conveying accurate or useful information to the caller. In some situations, the severity level of the incident may increase when dispatchers deviate from the script or proceed through the script too slowly.

Among other things, disclosed are a method, device, and system for an electronic digital assistant to evaluate compliance of communication of a dispatcher. The electronic digital assistant may determine a severity level of a call and take action when the severity level of the call exceeds a predetermined severity level threshold (for example, dispatching a public safety officer to the location of the incident). The electronic digital assistant may also monitor communication between the dispatcher and a caller and compare a characteristic of the monitored communication (for example, content of the communication) to a constraint of conversational procedure (for example, a script for the type of incident to which the call relates).

One embodiment provides an electronic computing device that includes an input device, a transceiver, and one or more electronic processors communicatively coupled to the transceiver. The one or more electronic processors are configured to monitor communication between a dispatcher and a caller during a call. The one or more electronic processors are further configured to determine a type of call based on one or more of the monitored communication and metadata received via the input device. The one or more electronic processors are further configured to determine a conversational procedure based on the type of call and compare a characteristic of the monitored communication to a constraint of the conversational procedure. The one or more electronic processors are further configured to determine that the characteristic of the monitored communication is outside the constraint of the conversational procedure. The one or more electronic processors are further configured to take an action as a function of determining that the characteristic of the monitored communication is outside the constraint of the conversational procedure.

Another embodiment provides a method of evaluating compliance of communication of a dispatcher. The method includes monitoring, with an electronic computing device, communication between the dispatcher and a caller during a call. The method further includes determining, with the electronic computing device, a type of call based on one or more of the monitored communication and metadata received via an input device. The method further includes determining, with the electronic computing device, a conversational procedure based on the type of call. The method further includes comparing, with the electronic computing device, a characteristic of the monitored communication to a constraint of the conversational procedure. The method further includes determining, with the electronic computing device, that the characteristic of the monitored communication is outside the constraint of the conversational procedure. The method further includes taking an action, with the electronic computing device, as a function of determining that the characteristic of the monitored communication is outside the constraint of the conversational procedure.

Each of the above-mentioned embodiments will be discussed in more detail below, starting with example communication system and device architectures of the system in which the embodiments may be practiced, followed by an illustration of processing steps for achieving the method, device, and system for an electronic digital assistant. Further advantages and features consistent with this disclosure will be set forth in the following detailed description, with reference to the figures.

1. Communication System and Device Structures a. Communication System Structure

Figure 1B:
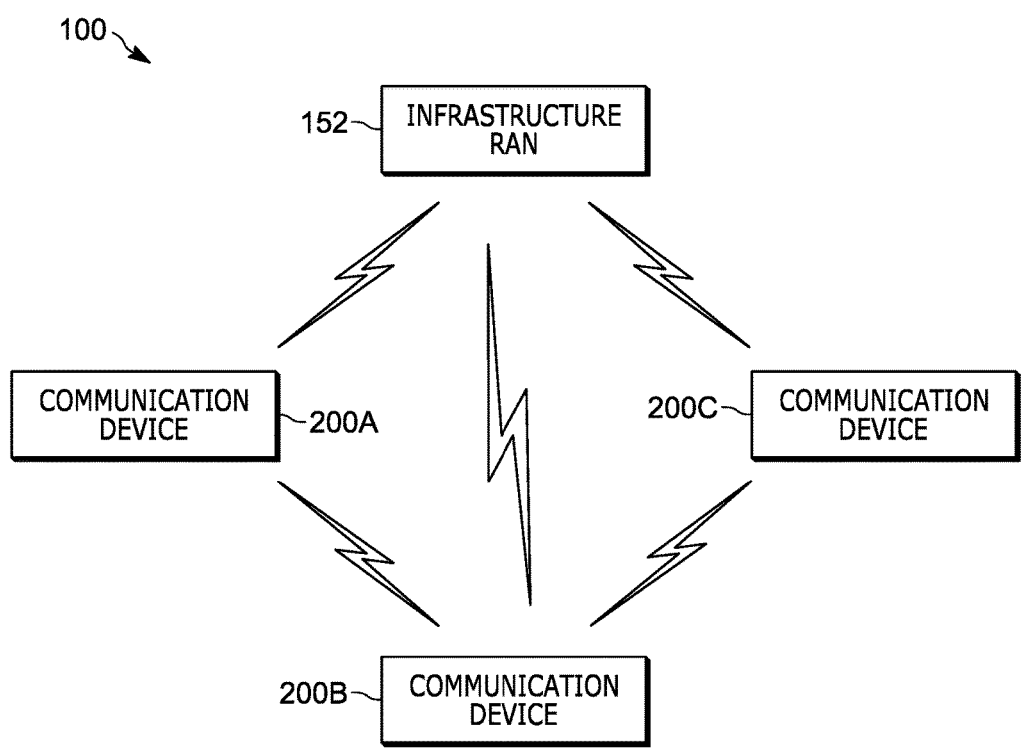

Referring now to the drawings, and in particular FIG. 1A, a communication system diagram illustrates a system 100 of devices including a first set of devices that a user 102 (illustrated in FIG. 1A as a first responder police officer) may wear, such as a primary battery-powered portable radio 104 used for narrowband and/or broadband direct-mode or infrastructure communications, a battery-powered radio speaker microphone (RSM) video capture device 106, a laptop 114 having an integrated video camera and used for data applications such as incident support applications, smart glasses 116 (for example, which may be virtual reality, augmented reality, or mixed reality glasses), sensor-enabled holster 118, and/or biometric sensor wristband 120. Although FIG. 1A illustrates only a single user 102 with a respective first set of devices, in other embodiments, the single user 102 may include additional sets of same or similar devices, and additional users may be present with respective additional sets of same or similar devices as indicated by FIG. 1B. In some embodiments, the system 100 includes one or more tablets, interactive whiteboards, and/or other interactive displays that include an input device that is sensitive to contact from, for example, a stylus or a user's finger (and that may be referred to as a touch sensitive display). In some embodiments, one or both of the portable radio 104 and the laptop 114 include a touch sensitive display.

System 100 may also include a vehicle 132 associated with the user 102 having an integrated mobile communication device 133, an associated vehicular video camera 134, and a coupled vehicular transceiver 136. Although FIG. 1A illustrates only a single vehicle 132 with a single mobile communication device 133, respective single vehicular video camera 134 and/or microphone, and a single coupled vehicular transceiver 136, in other embodiments, the vehicle 132 may include additional same or similar mobile communication devices, video cameras, microphones, and/or transceivers, and additional vehicles may be present with respective additional sets of mobile communication devices, video cameras, microphones, and/or transceivers. In some embodiments, the vehicle 132 may include one or more communication devices that include a touch sensitive display (for example, the mobile communication device 133).

Each of the portable radio 104, RSM video capture device 106, laptop 114, vehicular mobile communication device 133, and other devices may be capable of directly wirelessly communicating via direct-mode wireless link(s) 142, and/or may be capable of wirelessly communicating via a wireless infrastructure radio access network (RAN) 152 over respective wireless link(s) 140, 144 and via corresponding transceiver circuits. These devices may be referred to as communication devices and are configured to receive inputs associated with the user 102 and/or provide outputs to the user 102 in addition to communicating information to and from other communication devices and the infrastructure RAN 152.

The RAN 152 may be a wired or wireless communication network. All or parts of the RAN 152 may be implemented using various existing networks, for example, a land mobile radio (LMR) network, a Long Term Evolution (LTE) network, a Bluetooth™ network, a wireless local area network (for example, Wi-Fi), a Machine-to-machine (M2M) autonomous network, and a public switched telephone network. The RAN 152 may also include future developed networks. In some embodiments, the RAN 152 may also include a combination of the networks mentioned previously herein.

In the example of FIG. 1, the portable radio 104 may form the hub of communication connectivity for the user 102, through which other accessory devices, such as a biometric sensor (for example, the biometric sensor wristband 120), an activity tracker, a weapon status sensor (for example, the sensor-enabled holster 118), a heads-up-display (for example, the smart glasses 116), the RSM video capture device 106, and/or the laptop 114 may communicatively couple.

In order to communicate with and exchange video, audio, and other media and communications with the RSM video capture device 106, laptop 114, and/or smart glasses 116, the portable radio 104 may contain one or more physical electronic ports (such as a USB port, an Ethernet port, an audio jack, etc.) for direct electronic coupling with the RSM video capture device 106, laptop 114, and/or smart glasses 116. In some embodiments, the portable radio 104 may contain a short-range transmitter and/or transceiver for wirelessly coupling with the RSM video capture device 106, laptop 114, and/or smart glasses 116. The short-range transmitter may be a Bluetooth, Zigbee, or NFC transmitter having a transmit range on the order of 0.01-100 meters, or 0.1-10 meters. In other embodiments, the RSM video capture device 106, the laptop 114, and/or the smart glasses 116 may contain their own long-range transceivers and may communicate with one another and/or with the infrastructure RAN 152 or vehicular transceiver 136 directly without passing through portable radio 104.

The RSM video capture device 106 provides voice functionality features similar to a traditional RSM, including one or more of acting as a remote microphone that is closer to the user's 102 mouth, providing a remote speaker allowing playback of audio closer to the user's 102 ear, and including a PTT switch or other type of PTT input. The voice and/or audio recorded at the remote microphone may be provided to the portable radio 104 for storage and/or analysis or for further transmission to other mobile communication devices or the infrastructure RAN 152, or may be directly transmitted by the RSM video capture device 106 to other communication devices or to the infrastructure RAN 152. The voice and/or audio played back at the remote speaker may be received from the portable radio 104 or received directly from one or more other communication devices or the infrastructure RAN 152. The RSM video capture device 106 may include a separate physical PTT switch 108 that functions, in cooperation with the portable radio 104 or on its own, to maintain the portable radio 104 and/or RSM video capture device 106 in a monitor only mode, and which switches the device(s) to a transmit-only mode (for half-duplex devices) or transmit and receive mode (for full-duplex devices) upon depression or activation of the PTT switch 108. The portable radio 104 and/or RSM video capture device 106 may form part of a group communications architecture that allows a single communication device to communicate with one or more group members (not shown) associated with a particular group of devices at a same time.

Additional features may be provided at the RSM video capture device 106 as well. For example, a display screen 110 may be provided for displaying images, video, and/or text to the user 102 or to someone else. The display screen 110 may be, for example, a liquid crystal display (LCD) screen or an organic light emitting display (OLED) display screen. In some embodiments, a touch sensitive input interface may be incorporated into the display screen 110 as well, allowing the user 102 to interact with content provided on the display screen 110. A soft PTT input may also be provided, for example, via such a touch interface.

A video camera 112 may also be provided at the RSM video capture device 106, integrating an ability to capture images and/or video and store the captured image data (for further analysis) or transmit the captured image data as an image or video stream to the portable radio 104 and/or to other communication devices or to the infrastructure RAN 152 directly. The video camera 112 and RSM remote microphone may be used, for example, for capturing audio and/or video of a field-of-view associated with the user 102, perhaps including a suspect and the suspect's surroundings, storing the captured image and/or audio data for further analysis or transmitting the captured audio and/or video data as an audio and/or video stream to the portable radio 104 and/or to other communication devices or to the infrastructure RAN 152 directly for further analysis. An RSM remote microphone of the RSM video capture device 106 may be an omni-directional or unidirectional microphone or array of omni-directional or unidirectional microphones that may be capable of identifying a direction from which a captured sound emanated.

In some embodiments, the RSM video capture device 106 may be replaced with a more limited body worn camera that may include the video camera 112 and/or microphone noted above for capturing audio and/or video, but may forego one or more of the features noted above that transform the body worn camera into a more full featured RSM, such as the separate physical PTT switch 108 and the display screen 110, and remote microphone functionality for voice communications in cooperation with portable radio 104.

The laptop 114, in particular, may be any wireless communication device used for infrastructure RAN or direct-mode media communication via a long-range or short-range wireless transmitter with other communication devices and/or the infrastructure RAN 152. The laptop 114 includes a display screen for displaying a user interface to an operating system and one or more applications running on the operating system, such as a broadband PTT communications application, a web browser application, a vehicle history database application, a workflow application, a forms or reporting tool application, an arrest record database application, an outstanding warrant database application, a mapping and/or navigation application, a health information database application, and/or other types of applications that may require user interaction to operate. The laptop 114 display screen may be, for example, an LCD screen or an OLED display screen. In some embodiments, a touch sensitive input interface may be incorporated into the display screen as well, allowing the user 102 to interact with content provided on the display screen. A soft PTT input may also be provided, for example, via such a touch interface.

Front and/or rear-facing video cameras may also be provided at the laptop 114, integrating an ability to capture video and/or audio of the user 102 and the user's 102 surroundings, perhaps including a field-of-view of the user 102 and/or a suspect (or potential suspect) and the suspect's surroundings, and store and/or otherwise process the captured video and/or audio for further analysis or transmit the captured video and/or audio as a video and/or audio stream to the portable radio 104, other communication devices, and/or the infrastructure RAN 152 for further analysis.

The smart glasses 116 may include a digital imaging device, an electronic processor, a short-range and/or long-range transceiver device, and/or a projecting device. The smart glasses 116 may maintain a bi-directional connection with the portable radio 104 and provide an always-on or on-demand video feed pointed in a direction of the user's 102 gaze via the digital imaging device, and/or may provide a personal display via the projection device integrated into the smart glasses 116 for displaying information such as text, images, or video received from the portable radio 104 or directly from the infrastructure RAN 152. In some embodiments, the smart glasses 116 may include its own long-range transceiver and may communicate with other communication devices and/or with the infrastructure RAN 152 or vehicular transceiver 136 directly without passing through portable radio 104.

The sensor-enabled holster 118 may be an active (powered) or passive (non-powered) sensor that maintains and/or provides state information regarding a weapon or other item normally disposed within the user's 102 sensor-enabled holster 118. The sensor-enabled holster 118 may detect a change in state (presence to absence) and/or an action (removal) relative to the weapon normally disposed within the sensor-enabled holster 118. The detected change in state and/or action may be reported to the portable radio 104 via its short-range transceiver. In some embodiments, the sensor-enabled holster 118 may also detect whether the first responder's hand is resting on the weapon even if it has not yet been removed from the holster and provide such information to portable radio 104. In some embodiments, a weapon of the user 102 may include a sensor that detects when the weapon is discharged. The detected discharge may be reported to the portable radio 104, for example. Other possibilities exist as well.

The biometric sensor wristband 120 may be an electronic device for tracking an activity of the user 102 or a health status of the user 102, and may include one or more movement sensors (such as an accelerometer, magnetometer, and/or gyroscope) that may periodically or intermittently provide to the portable radio 104 indications of orientation, direction, steps, acceleration, and/or speed, and indications of health such as one or more of a captured heart rate, a captured breathing rate, and a captured body temperature of the user 102, perhaps accompanying other information. In some embodiments, the biometric sensor wristband 120 may include its own long-range transceiver and may communicate with other communication devices and/or with the infrastructure RAN 152 or vehicular transceiver 136 directly without passing through portable radio 104.

Although the biometric sensor wristband 120 is shown in FIG. 1A as a bracelet worn around the wrist, in other examples, the biometric sensor wristband 120 may additionally and/or alternatively be worn around another part of the body, or may take a different physical form including an earring, a finger ring, a necklace, a glove, a belt, or some other type of wearable, ingestible, or insertable form factor. In some embodiments, the biometric sensor wristband 120 or another device of the user 102 may detect characteristics of the environment of the user 102 (for example, temperature, humidity, air quality, and the like).

The portable radio 104, RSM video capture device 106, laptop 114, smart glasses 116, sensor-enabled holster 118, and/or biometric sensor wristband 120 may form a personal area network (PAN) via corresponding short-range PAN transceivers, which may be based on a Bluetooth, Zigbee, Bluetooth Low Energy, WiFi, Near Field Communication (NFC), Radio Frequency ID (RFID) or other short-range wireless protocol having a transmission range on the order of meters, tens of meters, or hundreds of meters.

The portable radio 104 and/or RSM video capture device 106 (or any other device in FIG. 1A, for that matter) may each include a location determination device integrated with or separately disposed in the portable radio 104 and/or RSM 106 and/or in respective receivers, transmitters, or transceivers of the portable radio 104 and RSM 106 for determining a location of the portable radio 104 and RSM 106. The location determination device may be, for example, a global positioning system (GPS) receiver or wireless triangulation logic using a wireless receiver or transceiver and a plurality of wireless signals received at the wireless receiver or transceiver from different locations, among other possibilities. The location determination device may also include an orientation sensor for determining an orientation that the device is facing. Each orientation sensor may include a gyroscope and/or a magnetometer. Other types of orientation sensors could be used as well. The location may then be stored locally or transmitted via the transmitter or transceiver to other communication devices and/or to the infrastructure RAN 152.

The vehicle 132 associated with the user 102 may include the mobile communication device 133, the vehicular video camera 134 and/or microphone, and the vehicular transceiver 136, all of which may be coupled to one another via a wired and/or wireless vehicle area network (VAN), perhaps along with other sensors physically or communicatively coupled to the vehicle 132. The vehicular transceiver 136 may include transceiver for directly wirelessly communicating with communication devices such as the portable radio 104, the RSM 106, and the laptop 114 via wireless link(s) 142 and/or for wirelessly communicating with the RAN 152 via wireless link(s) 144. The vehicular transceiver 136 may further communicate between the mobile communication device 133 and/or the vehicular video camera 134 in the VAN. The mobile communication device 133 may, in some embodiments, include the vehicular transceiver 136 and/or the vehicular video camera 134 integrated therewith, and may operate to store and/or process video and/or audio produced by the video camera 134 and/or transmit the captured video and/or audio as a video and/or audio stream to the portable radio 104, other communication devices, and/or the infrastructure RAN 152 for further analysis. A microphone (not shown), or an array thereof, may be integrated in the video camera 134 and/or at the mobile communication device 133 (or additionally or alternatively made available at a separate location of the vehicle 132) and communicatively coupled to the mobile communication device 133 and/or vehicular transceiver 136 for capturing audio and storing, processing, and/or transmitting the audio in a same or similar manner to the video as set forth above.

The vehicle 132 may be a human-operable vehicle, or may be a self-driving vehicle operable under control of the mobile communication device 133 perhaps in cooperation with video camera 134 (which may include a visible-light camera, an infrared camera, a time-of-flight depth camera, and/or a light detection and ranging (LiDAR) device). Command information and/or status information such as location and speed may be exchanged with the self-driving vehicle via the VAN and/or the PAN (when the PAN is in range of the VAN or via the VAN's infrastructure RAN link). In some embodiments, devices within the vehicle 132 may communicate with devices in other vehicles via a Vehicular to Vehicular (V2V) Network.

The vehicle 132 and/or transceiver 136, similar to the portable radio 104 and/or respective receivers, transmitters, or transceivers thereof, may include a location (and/or orientation) determination device integrated with or separately disposed in the mobile communication device 133 and/or transceiver 136 for determining (and storing and/or transmitting) a location (and/or orientation) of the vehicle 132.

In some embodiments, instead of a vehicle 132, a land, air, or water-based drone with the same or similar audio and/or video and communications capabilities and the same or similar self-navigating capabilities as set forth above may be disposed, and may similarly communicate with the user's 102 PAN and/or with the infrastructure RAN 152 to support the user 102 in the field.

The VAN may communicatively couple with the PAN disclosed above when the VAN and the PAN come within wireless transmission range of one another, perhaps after an authentication takes place there between. In some embodiments, one of the VAN and the PAN may provide infrastructure communications to the other, depending on the situation and the types of devices in the VAN and/or PAN and may provide interoperability and communication links between devices (such as video cameras) and sensors within the VAN and PAN.

Although the RSM 106, the laptop 114, and the vehicle 132 are illustrated in FIG. 1A as providing example video cameras and/or microphones for use in capturing audio and/or video streams, other types of cameras and/or microphones could be used as well, including but not limited to, fixed or pivotable video cameras secured to lamp posts, automated teller machine (ATM) video cameras, other types of body worn cameras such as head-mounted cameras, other types of vehicular cameras such as roof-mounted cameras, or other types of audio and/or video recording devices accessible via a wired or wireless network interface same or similar to that disclosed herein.

In some embodiments, one or more of the user 102, the vehicle 132, the portable radio 104, the RSM video capture device 106, and any other device in FIG. 1A may be equipped with an environmental sensor such as a chemical, biological, radiological, nuclear, or explosive (CBRNE) sensor. Measurements made by the CBRNE sensor may be stored locally or transmitted via a transmitter or transceiver to other communication devices and/or to the infrastructure RAN 152.

The system of FIG. 1A includes a dispatch console 158 operated by a dispatcher. The dispatch console 158 may include one or more of the devices described above with respect to the user 102. For example, the dispatch console 158 may include a laptop 114 or another computer with input devices and a display. In some embodiments, the dispatch console 158 includes a portable radio 104 or a stationary radio that functions similarly to the portable radio 104. In some embodiments, the dispatch console 158 is coupled to a telephone line to allow the dispatcher to receive calls from public citizens. In some embodiments, the dispatch console 158 includes a headset coupled to the portable radio 104 or stationary radio. The headset may be worn by the dispatcher to allow the dispatcher to communicate with callers in a hands-free manner that allows the dispatcher to simultaneously operate the laptop 114 or another computer during a call. Other possibilities for devices included in the dispatch console 158 are possible. While the dispatch console 158 was described above with reference to a single dispatcher, in some embodiments, the dispatch console 158 is located at dispatch center that includes a plurality of dispatch consoles 158 that are each operated by one or more dispatchers.

The infrastructure RAN 152 is illustrated in FIG. 1A as providing coverage for the portable radio 104, RSM video capture device 106, laptop 114, smart glasses 116, and/or vehicle transceiver 136 via a single fixed terminal 154 coupled to a single infrastructure controller 156 (for example, a radio controller, call controller, PTT server, zone controller, MME, BSC, MSC, site controller, Push-to-Talk controller, or other network device) and including the dispatch console 158 operated by the dispatcher. In other embodiments, additional fixed terminals and additional controllers may be disposed to support a larger geographic footprint and/or a larger number of mobile devices. In some embodiments, a middleware server that translates between a narrowband system and a broadband system is disposed in infrastructure RAN 152 at infrastructure controller 156 or at a separate cloud computing cluster 162 communicably coupled to infrastructure controller 156 via internet protocol (IP) network 160, among other possibilities.

The infrastructure controller 156 illustrated in FIG. 1A, or some other back-end infrastructure device or combination of back-end infrastructure devices existing on-premises or in the remote cloud computing cluster 162 accessible via the IP network 160 (such as the Internet), may additionally or alternatively operate as a back-end electronic digital assistant, a back-end audio and/or video processing device, and/or a remote cloud-based storage device consistent with the remainder of this disclosure.

The IP network 160 may comprise one or more routers, switches, LANs, WLANs, WANs, access points, or other network infrastructure, including but not limited to, the public Internet. The cloud computing cluster 162 may be comprised of a plurality of computing devices, such as the one set forth in FIG. 2, one or more of which may be executing none, all, or a portion of an electronic digital assistant service, sequentially or in parallel, across the one or more computing devices. The one or more computing devices comprising the cloud computing cluster 162 may be geographically co-located or may be separated by inches, meters, or miles, and inter-connected via electronic and/or optical interconnects. Although not shown in FIG. 1A, one or more proxy servers or load balancing servers may control which one or more computing devices perform any part or all of the electronic digital assistant service.

As shown in FIG. 1A, database(s) 164 may be accessible via the IP network 160 and/or the cloud computing cluster 162, and may include databases such as a long-term video storage database, a historical or forecasted weather database, an offender database perhaps including facial recognition images to match against, a cartographic database of streets and elevations, a traffic database of historical or current traffic conditions, or other types of databases. Databases 164 may further include all or a portion of the databases described herein as being provided at the infrastructure controller 156. In some embodiments, the databases 164 may be maintained by third parties (for example, the National Weather Service or a Department of Transportation, respectively). As shown in FIG. 1A, the databases 164 are communicatively coupled with the infrastructure RAN 152 to allow the communication devices (for example, the portable radio 104, the RSM video capture device 106, the laptop 114, the mobile communication device 133, and the dispatch console 158) to communicate with and retrieve data from the databases 164 via infrastructure controller 156 and IP network 160. In some embodiments, the databases 164 are commercial cloud-based storage devices. In some embodiments, the databases 164 are housed on suitable on-premises database servers. The databases 164 of FIG. 1A are merely examples. In some embodiments, the system 100 additionally or alternatively includes other databases that store different information. In some embodiments, the databases 164 and/or additional or other databases are integrated with, or internal to, the infrastructure controller 156.

Finally, although FIG. 1A describes a communication system 100 generally as a public safety communication system that includes a user 102 generally described as a police officer and a vehicle 132 generally described as a police cruiser, in other embodiments, the communication system 100 may additionally or alternatively be a retail communication system including a user 102 that may be an employee of a retailer and a vehicle 132 that may be a vehicle for use by the user 102 in furtherance of the employee's retail duties (for example, a shuttle or self-balancing scooter). In other embodiments, the communication system 100 may additionally or alternatively be a warehouse communication system including a user 102 that may be an employee of a warehouse and a vehicle 132 that may be a vehicle for use by the user 102 in furtherance of the employee's retail duties (for example, a forklift). In still further embodiments, the communication system 100 may additionally or alternatively be a private security communication system including a user 102 that may be an employee of a private security company and a vehicle 132 that may be a vehicle for use by the user 102 in furtherance of the private security employee's duties (for example, a private security vehicle or motorcycle). In even further embodiments, the communication system 100 may additionally or alternatively be a medical communication system including a user 102 that may be a doctor or nurse of a hospital and a vehicle 132 that may be a vehicle for use by the user 102 in furtherance of the doctor or nurse's duties (for example, a medical gurney or ambulance). In still another example embodiment, the communication system 100 may additionally or alternatively be a heavy machinery communication system including a user 102 that may be a miner, driller, or extractor at a mine, oil field, or precious metal or gem field and a vehicle 132 that may be a vehicle for use by the user 102 in furtherance of the miner, driller, or extractor's duties (for example, an excavator, bulldozer, crane, front loader). Other possibilities exist as well.

As mentioned previously, many of the devices shown in FIG. 1A (such as the portable radio 104, the RSM video capture device 106, the laptop 114, the mobile communication device 133, the infrastructure controller 156, the dispatch console 158, and one or more computing devices in the cloud computing cluster 162) may be referred to as communication devices (for example, a communication device 200 as explained below with respect to FIG. 2). Although FIG. 1A shows multiple communication devices 200 associated with the user 102, in some embodiments, the communication system 100 includes communication devices 200 of multiple users. For example, as shown in FIG. 1B, the communication device 200A is associated with a first user, the communication device 200B is associated with a second user, and the communication device 200C is associated with a third user. As indicated by FIG. 1B, in some embodiments, the communication devices 200A, 200B, and 200C communicate with each other over the infrastructure RAN 152 and/or communicate with each other directly as described previously herein. In some embodiments, one or more users may have multiple associated communication devices 200, for example, as shown in FIG. 1A. In some embodiments, the dispatch console 158 (which also may be referred to as a communication device 200) may directly communicate with other communication devices 200 of multiple users through the infrastructure RAN 152. For example, the dispatch console 158 communicates with one or more of the portable radio 104, the RSM video capture device 106, the laptop 114, the smart glasses 116, and/or the vehicle transceiver 136. In some embodiments, the dispatch console 158 also communicates with the cloud computing cluster 162, and the database(s) 164. In some embodiments, the dispatch console 158 communicates with another dispatch console 158. For example, the dispatch console 158 is located within a first dispatch center (for example, a county-wide or state-wide general dispatch center) and communicates with another dispatch console 158 located at a second dispatch center (for example, a police station of city, a fire station of a city or predefined geographical area within the city, and the like). In other words, in some embodiments, the dispatch console 158 communicates with a public safety command center.

b. Device Structure

Figure 2:
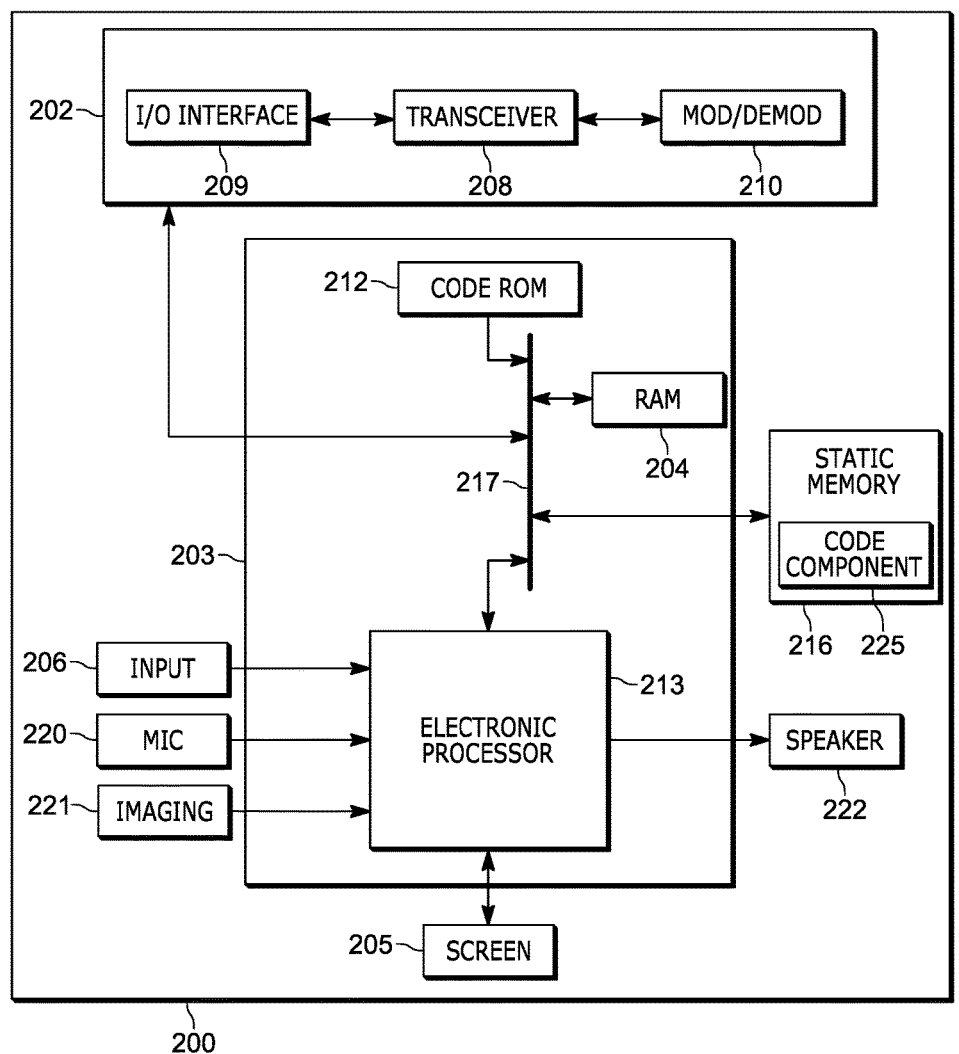
FIG. 2 is a device diagram showing a device structure of a communication device of the system of FIGS. 1A and 1B in accordance with some embodiments.

FIG. 2 sets forth a schematic diagram that illustrates a communication device 200 according to some embodiments of the present disclosure. The communication device 200 may be, for example, embodied in the portable radio 104, the RSM video capture device 106, the laptop 114, the mobile communication device 133, the infrastructure controller 156, the dispatch console 158, one or more computing devices in the cloud computing cluster 162, or some other communication device not illustrated in FIG. 1A, and/or may be a distributed communication device across two or more of the foregoing (or multiple of a same type of one of the foregoing) and linked via a wired and/or wireless communication link(s). In some embodiments, the communication device 200 (for example, the portable radio 104) may be communicatively coupled to other devices such as the sensor-enabled holster 118 as described above. In such embodiments, the combination of the portable radio 104 and the sensor-enabled holster 118 may be considered a single communication device 200.

While FIG. 2 represents the communication devices described above with respect to FIGS. 1A and 1B, depending on the type of the communication device, the communication device 200 may include fewer or additional components in configurations different from that illustrated in FIG. 2. For example, in some embodiments, the communication device 200 acting as the infrastructure controller 156 may not include one or more of the screen 205, microphone 220, imaging device 221, and speaker 222. As another example, in some embodiments, the communication device 200 acting as the portable radio 104 or the RSM video capture device 106 may further include a location determination device (for example, a global positioning system (GPS) receiver) as explained above. Other combinations are possible as well.

As shown in FIG. 2, the communication device 200 includes a communications unit 202 coupled to a common data and address bus 217 of a processing unit 203 that includes an electronic processor 213. The communication device 200 may also include one or more input devices (for example, a keypad, pointing device, a button, a microphone 220, an imaging device 221, and/or another input device 206), each coupled to be in communication with the processing unit 203. In some instances, one or more communication devices 200 include a screen 205 that, in some embodiments, is a touch sensitive screen and thus also acts as an input device.

The microphone 220 may be present for capturing audio from a user and/or other environmental or background audio that is further processed by processing unit 203 in accordance with the remainder of this disclosure and/or is transmitted as voice or audio stream data, or as acoustical environment indications, by communications unit 202 to other portable radios and/or other communication devices. For example, the microphone 220 of the dispatch console 158 captures audio corresponding to communication between a dispatcher and a caller during a call as will be described in greater detail below. The imaging device 221 may provide video (still or moving images) of an area in a field of view of the communication device 200 for further processing by the processing unit 203 and/or for further transmission by the communications unit 202. A speaker 222 may be present for reproducing audio that is decoded from voice or audio streams of calls received via the communications unit 202 from public citizens or from other portable radios, from digital audio stored at the communication device 200, from other ad-hoc or direct mode devices, and/or from an infrastructure RAN device, or may playback alert tones or other types of pre-recorded audio.

The processing unit 203 may include a code Read Only Memory (ROM) 212 coupled to the common data and address bus 217 for storing data for initializing system components. The processing unit 203 may further include the electronic processor 213 (for example, a microprocessor or another electronic device) coupled, by the common data and address bus 217, to a Random Access Memory (RAM) 204 and a static memory 216.

The communications unit 202 may include one or more wired and/or wireless input/output (I/O) interfaces 209 that are configurable to communicate with other communication devices, such as a the portable radio 104, the laptop 114, the wireless RAN 152, the mobile communication device 133, the remote could computing cluster 162, the databases 164, and other dispatch consoles 158.

For example, the communications unit 202 may include one or more wireless transceivers 208 configurable to communicate via a wireless radio network. The communications unit 202 may additionally or alternatively include one or more wireline transceivers 208, such as an Ethernet transceiver, a USB transceiver, or similar transceiver configurable to communicate via a twisted pair wire, a coaxial cable, a fiber-optic link, or a similar physical connection to a wireline network. The transceiver 208 is also coupled to a combined modulator/demodulator 210.

The electronic processor 213 has ports for coupling to the screen 205, the microphone 220, the imaging device 221, the other input device 206, and/or the speaker 222. Static memory 216 may store operating code 225 for the electronic processor 213 that, when executed, performs one or more of the steps set forth in FIGS. 3 and 4 and the accompanying text. In some embodiments, the static memory 216 may store scripts corresponding to predetermined public safety incidents (for example, a cardiopulmonary resuscitation guide) to be used by dispatchers when handling calls from public citizens as described above and as will be described in greater detail below. The static memory 216 may comprise, for example, a hard-disk drive (HDD), an optical disk drive such as a compact disk (CD) drive or digital versatile disk (DVD) drive, a solid state drive (SSD), a tape drive, a flash memory drive, or a tape drive, and the like.

2. Processes for Evaluating Compliance of Communication of a Dispatcher

In some embodiments, an individual component and/or a combination of individual components of the system 100 may be referred to as an electronic computing device that implements an electronic digital assistant as mentioned above. For example, the electronic computing device may be a single electronic processor (for example, the electronic processor 213 of a dispatch console 158). In other embodiments, the electronic computing device includes multiple electronic processors distributed remotely from each other. For example, the electronic computing device may be implemented on a combination of at least two of the electronic processor 213 of the dispatch console 158, the electronic processor 213 of the infrastructure controller 156, and the electronic processor 213 of a back-end device in the cloud computing cluster 162 accessible via the IP network 160.

As one way to use the electronic digital assistant implemented by the electronic computing device, the microphone 220 of the dispatch console 158 may monitor communication between a dispatcher and a caller during a call. The electronic computing device receives audio signals representative of the communication between the dispatcher and the caller from the microphone 220 and analyzes the audio signals to determine the content of the communication between the dispatcher and the caller. For example, the electronic computing device may include a natural language processing (NLP) engine configured to determine the intent and/or content of a query from the caller. The electronic computing device may also be configured to determine a response to the query (for example, by retrieving stored data or by requesting data from a database such as one of the databases 164) and provide the response to an output device of the communication device 200 (for example, the screen 205 via a generated text-based response). In other words, one or more of the communication devices 200, embodied in one or more of the communication devices of FIG. 1A, such as the dispatch console 158, the infrastructure controller 156, and/or the cloud computing cluster 162 may include a natural language processing engine to analyze communication monitored by the microphone 220 of the dispatch console 158 and provide information or assistance to the dispatcher during a call.

Although monitoring of oral communication is described above, in some embodiments, the electronic computing device receives and responds to other types of inputs. For example, the dispatcher may input metadata into the electronic computing device during a call by typing text into a hard keyboard input device or a soft keyboard input provided on the screen 205 of the dispatch console 158. For example, the dispatcher may enter the name of a caller, the location of a caller, details of the incident about which the caller is calling, and the like. The electronic computing device may use this metadata to, for example, determine a type of call as explained in greater detail below.

As mentioned above, depending on the severity level of an incident in which a caller is calling for assistance, the speed at which information from the call is relayed to a third party (for example, a first responder) may be important. Additionally, when dispatchers deviate from a pre-approved script or proceed through the script too slowly, it may be indicative that the caller does not understand the information that the dispatcher is attempting to convey or that the dispatcher is not conveying accurate or useful information to the caller. In some situations, the severity level of the incident may increase when dispatchers deviate from the script or proceed through the script too slowly.

Figure 3:
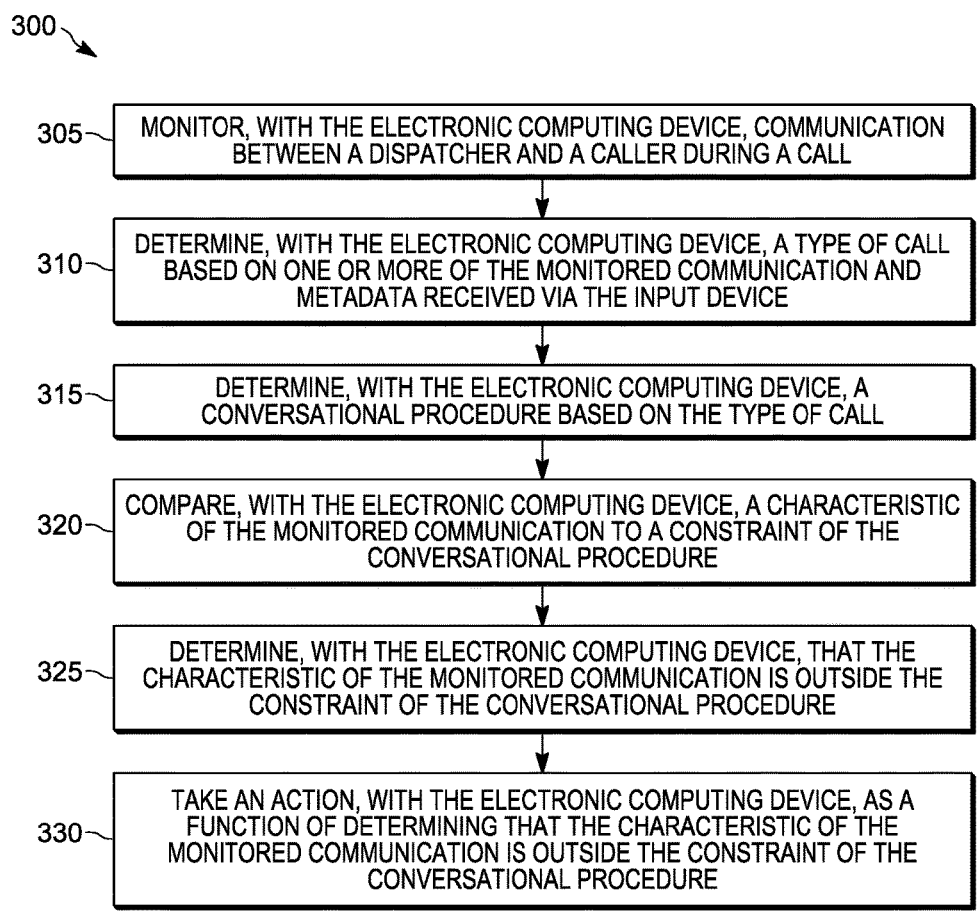
FIG. 3 illustrates a flow chart of a method of evaluating compliance of communication of a dispatcher in accordance with some embodiments.

To avoid and solve these problems, the electronic computing device that implements the electronic digital assistant may perform a method 300 illustrated in FIG. 3 to evaluate compliance of communication of a dispatcher and take assistive or corrective action in various situations. Among other things, the method 300 may provide a technical solution to a technical problem by reducing call backlog that may be caused by high severity calls or a lack of compliance with a script by a dispatcher. In other words, by taking assistive or corrective action for high severity calls or improperly-handled calls, the method 300 reduces call backlog and network congestion that may decrease the performance of the infrastructure RAN 152 in some situations.

FIG. 3 illustrates a flow chart diagram of the method 300 performed by the electronic computing device for evaluating compliance of communication of a dispatcher. While a particular order of processing steps, message receptions, and/or message transmissions is indicated in FIG. 3 as an example, timing and ordering of such steps, receptions, and transmissions may vary where appropriate without negating the purpose and advantages of the examples set forth in detail throughout the remainder of this disclosure.

At block 305, the electronic computing device monitors communication between a dispatcher and a caller during a call. For example, as described above, the electronic computing device may include a natural language processing engine to analyze audio signals of the monitored communication from the microphone 220 of the dispatch console 158 to determine the content of the monitored communication between the dispatcher and the caller. In some embodiments, the electronic computing device is configured to recognize a name of the caller, a location of the caller, a health status of the caller or of a victim (for example, a gunshot wound of the caller or victim, whether the victim is breathing, whether the victim is conscious, and the like), words related to an incident about which the caller is calling (for example, "fire," "hostage," "robbery," and the like), other keywords that may be used to populate information fields in an incident report, and the like. As mentioned above, in some embodiments, the electronic computing device receives metadata from an input device of the dispatch console 158 operated by the dispatcher. For example, the dispatcher may input metadata that is similar to the example information described above by typing the metadata into a hard keyboard input device or a soft keyboard input provided on the screen 205 of the dispatch console 158. In some embodiments, the input device may receive a selection of metadata by the dispatcher, for example, from a list of common incidents. For example, the input device may receive a selection from the dispatcher that indicates the caller is calling about a fire.

At block 310, the electronic computing device determines a type of call based on one or more of the monitored communication and the metadata received via the input device of the dispatch console 158. In some embodiments, the type of call defines the type of information and/or assistance that the caller is seeking. For example, the electronic computing device may determine that the type of call is a call relating to a fire when the electronic computing device determines that the caller has said the word "fire" multiple times during the monitored communication. As another example, the electronic computing device may determine that the type of call is a call relating to a heart attack when the caller has said the words "chest pain" and "can't breathe." As yet another example, the electronic computing device may determine that the type of call is a call where the caller seeks instructions on how to perform cardiopulmonary resuscitation when metadata corresponding to a cardiopulmonary resuscitation incident is selected or input by the dispatcher on an input device of the dispatch console 158. In some embodiments, the electronic computing device analyzes both the monitored communication and the metadata to determine the type of call.

At block 315, the electronic computing device determines a conversational procedure based on the type of call. As mentioned above, the static memory 216 may store scripts (for example, a cardiopulmonary resuscitation guide) to be used by dispatchers when handling calls. In some embodiments, the scripts include a list of questions or information that is to be conveyed by the dispatcher to the caller. With reference to the cardiopulmonary resuscitation guide example, the corresponding script may include a list of ordered tasks for the dispatcher to provide to the caller to properly perform cardiopulmonary resuscitation on a victim. The scripts for different incidents may be of different length. For example, the cardiopulmonary resuscitation script may be longer than a script that explains the tasks for handling a first degree burn on a victim.

After determining the conversational procedure based on the type of call, in some embodiments, the electronic computing device provides the conversational procedure (in other words, the script) to an output device of a communication device 200 of the dispatcher (in other words, the dispatch console 158). For example, the electronic computing device may display the conversational procedure on the screen 205 such that the dispatcher may view the conversational procedure during the call and convey information included in the conversational procedure to the caller.

At block 320, the electronic computing device compares a characteristic of the monitored communication to a constraint of the conversational procedure. In some embodiments, the characteristic of the monitored communication includes content of the monitored communication as articulated by the dispatcher. In other words, the electronic computing device may monitor the content being conveyed to the caller by the dispatcher. In some embodiments, the constraint of the conversational procedure may include a list and order of content (in other words, a list and order of tasks) that is to be articulated by the dispatcher. By comparing the words spoken by the dispatcher to the words of the conversational procedure, the electronic computing device is able to determine whether the dispatcher is deviating from the conversational procedure. In some embodiments, the electronic computing device determines whether the words spoken by the dispatcher have similar meaning as the words of the conversational procedure (for example, use of synonyms when conveying information). In some embodiments, the electronic computing device determines whether the dispatcher is conveying the tasks listed in the conversational procedure in the proper order. For example, the electronic computing device may provide a notification on the screen 205 when the electronic computing device determines that a task of the conversational procedure has been skipped by the dispatcher.

In some embodiments, the characteristic of the monitored communication includes an amount of time that has elapsed since the beginning of the call. In other words, the electronic computing device may monitor an amount of time that it takes the dispatcher to convey information included in one or more tasks of the conversational procedure or to receive information from the caller to complete one or more tasks of the conversational procedure. For example, the electronic computing device may analyze the words spoken by the dispatcher using the natural language processing engine to determine which task of the conversational procedure the dispatcher is currently attempting to complete. In some embodiments, the constraint of the conversational procedure may include an expected amount of time for the dispatcher to articulate predetermined content of the conversational procedure or complete predetermined tasks of the conversational procedure (such as receiving certain information from the caller). In some embodiments, the electronic computing device determines the expected amount of time for the dispatcher to articulate predetermined content or complete predetermined tasks of the conversational procedure by determining a length of a list of tasks of the conversational procedure and an estimated amount of time to complete each task on the list. By comparing the amount of time that has elapsed since the beginning of the call with the expected amount of time for the dispatcher to articulate or receive information included in one or more tasks, the electronic computing device is able to determine whether the speed at which the dispatcher is proceeding through the conversational procedure is slower than desired or faster than desired.

Although the above example monitors time elapsed since the beginning of the call, in some embodiments, time may be monitored at additional or different intervals. For example, the electronic computing device may monitor the time taken for the dispatcher to perform each task of the conversational procedure. In some embodiments, the electronic computing device may determine a predicted amount of time that the dispatcher is on pace to take to complete the tasks of the conversational procedure. For example, the electronic computing device may make this determination based on an amount of time it has taken the dispatcher to proceed through one or more of the first tasks of the conversational procedure and the expected amount of time to perform each of the tasks that have already been performed and each of the tasks that have yet to be performed. Such a determination is another example technique that the electronic computing device may use to determine the speed at which the dispatcher is proceeding through the conversational procedure.

At block 325, the electronic computing device determines that the characteristic of the monitored communication is outside the constraint of the conversational procedure. When the characteristic of the monitored communication includes the content of the monitored communication as articulated by the dispatcher, the electronic computing device determines that the words spoken by the dispatcher have a different meaning than the words of the conversational procedure. In some embodiments, the electronic computing devices makes this determination when a predetermined percentage of words spoken by the dispatcher do not correspond to at least one of the words of the conversational procedure or synonyms of the words of the conversational procedure. In some embodiments, the natural language processing engine may analyze the words spoken by the dispatcher to determine whether the content of the words spoken by the dispatcher corresponds to the words of the conversational procedure.

When the characteristic of the monitored communication includes the amount of time that has elapsed since the beginning of the call, the electronic computing device may determine that the speed at which the dispatcher is proceeding through the conversational procedure is slower than a desired speed. In some embodiments, the electronic computing device may determine that the speed at which the dispatcher is proceeding through the conversational procedure is slower than the desired speed by a predetermined amount (for example, by one minute or the like). In such embodiments, the electronic computing device allows the dispatcher to proceed through the conversational procedure at a speed that is slower than desired but may take action (at block 330) when the speed at which the dispatcher is proceeding through the conversational procedure is slower than the desired speed by a predetermined amount. In such embodiments, when the electronic computing device determines that the dispatcher is, for example, one minute behind the desired speed for proceeding through the conversational procedure, the electronic computing device determines that the characteristic of monitored communication is outside the constraint of the conversational procedure.

In some embodiments, the electronic computing device compares multiple characteristics of the monitored communication to respective constraints of the conversational procedure. For example, the electronic computing device may determine that both the content of the monitored communication as articulated by the dispatcher and the amount of time that has elapsed since the beginning of the call are outside the respective constraints of the conversational procedure (at block 325). Continuing this example, because the electronic computing device is monitoring multiple characteristics of the monitored communication, the electronic computing device may use less stringent individual constraints of the conversational procedure than when a single characteristic of the monitored communication is compared to its constraint of the conversational procedure. For example, the electronic computing device may proceed to block 330 to take action when the dispatcher is deviating from the conversational procedure in only a minor manner and when the dispatcher is also, for example, thirty seconds behind the desired speed for proceeding through the conversational procedure.

In some embodiments, the method 300 remains at block 320 to continue comparing the characteristic of the monitored communication to the constraint of the conversational procedure until the electronic computing device determines that the characteristic of the monitored communication is outside the constraint of the conversational procedure (at block 325).

At block 330, the electronic computing device takes an action as a function of determining that the characteristic of the monitored communication is outside the constraint of the conversational procedure. In some embodiments, the action includes the electronic computing device transmitting, via the transceiver 208 for example, information gathered from the monitored communication to a communication device 200 of a first responder as a function of determining that the characteristic of the monitored communication is outside the constraint of the conversational procedure. For example, the electronic computing device may transmit the location of the incident and the type of incident to the communication device 200 of the first responder while the dispatcher is still communicating with the caller. In this example, the dispatcher is able to continue to communicate and provide instructions to the caller and does not have to hold communication with the caller to dispatch the first responder to the location of the incident. In other words, the electronic computing device transmits information to the communication device 200 of the first responder in parallel with the dispatcher communicating with the caller. Other examples of information gathered from the monitored communication that may be transmitted to the communication device 200 of the first responder include a name of the caller, a health status of the caller, and a health status of a victim about whom the caller is calling. In some embodiments, the electronic computing device may determine a recommended route to the location of the caller from a location of the communication device 200 of the first responder. In such embodiments, the electronic computing device may transmit the recommended route to the communication device 200 of the first responder. In some embodiments, the electronic computing device may additionally or alternatively transmit the metadata entered by the dispatcher to the communication device 200 of the first responder.

In some embodiments, the information transmitted to the communication device 200 of the first responder is transmitted directly from the dispatch console 158, via the RAN 152, to the communication device 200 of the first responder. In other embodiments, the information transmitted to the communication device 200 of the first responder is transmitted indirectly. For example, the dispatch console 158 may transmit the information to a public safety command center (for example, a police station, a fire station, and the like) that forwards the information to the communication device 200 of the first responder via the RAN 152.

In some embodiments, the action taken by the electronic computing device (at block 330) includes providing additional and/or different content for at least some of the questions and/or information included in the conversational procedure. For example, when the electronic computing device determines that the dispatcher has repeated the same information several times, the electronic computing device may provide such information in a rephrased manner and/or may provide additional details on such information. In other words, the electronic computing device may provide additional and/or different content to an output device of the communication device 200 of the dispatcher that may allow the caller to better understand the information attempted to be conveyed to the caller. As one example, when assisting the caller with a situation involving cardiopulmonary resuscitation, the conversational procedure instructs the dispatcher to instruct the caller to "pump the victim's chest." However, the caller may not understand this instruction so the dispatcher may repeat the same instruction several times. After the electronic computing device determines that the dispatcher has repeated the same instruction, for example, four times, the electronic computing device may change the instruction to instruct the dispatcher to say, "place your hands on the victim's chest and push down quickly for approximately one half of a second." In this example, the changed instruction may allow the caller to understand the dispatcher such that the dispatcher may continue to proceed through the conversational procedure.

In some embodiments, the action taken by the electronic computing device (at block 330) includes switching the call between the dispatcher and the caller to a communication device 200 of a second dispatcher (in other words, a second dispatch console 158) as a function of determining that the characteristic of the monitored communication is outside the constraint of the conversational procedure. For example, when the electronic computing device determines that the dispatcher has been unable to complete the first task of the conversational procedure (for example, obtaining the name or location of the caller) within a predetermined amount of time, the electronic computing device may switch the call to another dispatch console 158 to be handled by another dispatcher. In some situations, switching dispatchers may allow the second dispatcher and the caller to better understand each other such that information is obtained from the caller more quickly.

In some embodiments, the action taken by the electronic computing device (at block 330) includes providing a notification on an output device (for example, the screen 205) as a function of determining that the characteristic of the monitored communication is outside the constraint of the conversational procedure. For example, as described above, the electronic computing device may provide a notification on the screen 205 when the electronic computing device determines that a task of the conversational procedure has been skipped by the dispatcher. Such a notification may remind the dispatcher to return to and complete the skipped task before proceeding with the remainder of the conversational procedure. As another example, the electronic computing device may provide a notification on the screen 205 when the speed at which the dispatcher is proceeding through the conversational procedure is slower than desired. Such a notification may prompt the dispatcher to attempt to acquire information from the caller more quickly and proceed through the conversational procedure more quickly. In some embodiments, when the electronic computing device transmits information to a communication device 200 of a first responder or switches the call to a communication device 200 of a second dispatcher, the electronic computing device also provides a notification on the screen 205 to notify the dispatcher of such action. In other embodiments, the electronic computing device does not provide a notification to the dispatcher in such situations.

As explained above, in some situations, the dispatcher deviating from the conversational procedure and/or proceeding through the conversational procedure at a slower speed than desired may be indicative that the caller does not understand the information that the dispatcher is attempting to convey or that the dispatcher is not conveying accurate or useful information to the caller. Such calls may take longer than expected or desired to be handled by the dispatcher and may cause call backlog and network congestion that may decrease the performance of the infrastructure RAN 152 in some situations. Accordingly, when the electronic computing device takes action as a function of determining that the characteristic of the monitored communication is outside the constraint of the conversational procedure (at block 330), such action reduces the call backlog and network congestion on the infrastructure RAN 152 by assisting dispatchers to complete calls they are handling more quickly.

Figure 4:
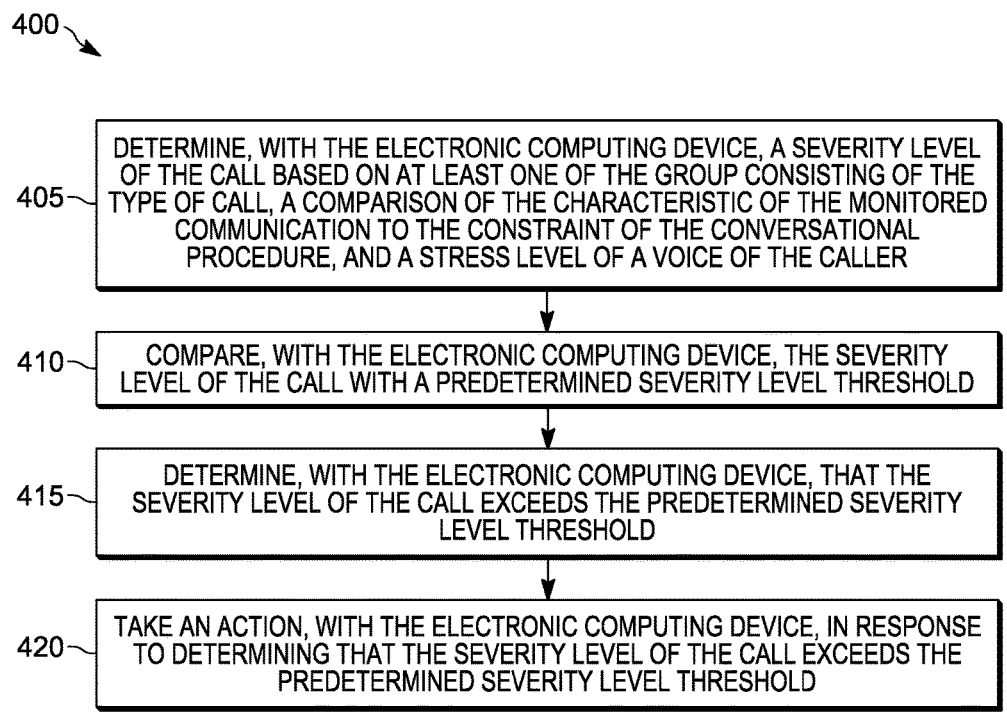
FIG. 4 illustrates a flow chart of a method of determining a severity level of a call between a dispatcher and a caller and taking an action to assist the dispatcher when the severity level exceeds a predetermined severity level threshold in accordance with some embodiments.

As another way to solve the above technological problem in a similar manner, the electronic computing device that implements the electronic digital assistant may additionally or alternatively perform a method 400 illustrated in a flowchart diagram of FIG. 4. The method 400 is executed by the electronic computing device to determine a severity level of a call and take an action to assist the dispatcher when the severity level exceeds a predetermined severity level threshold. In some embodiments, the method 300 may be at least partially performed as a sub-method within the method 400 as explained below. While a particular order of processing steps, message receptions, and/or message transmissions is indicated in FIG. 4 as an example, timing and ordering of such steps, receptions, and transmissions may vary where appropriate without negating the purpose and advantages of the examples set forth in detail throughout the remainder of this disclosure.

At block 405, the electronic computing device determines a severity level of a call between the dispatcher and a caller based on at least one of the group consisting of a type of call, a comparison of a characteristic of the monitored communication to a constraint of a conversational procedure, and a stress level of a voice of the caller. In some embodiments, when executing block 405, the electronic computing device performs similar functions as described above with respect to blocks 305, 310, 315, and 320 of the method 300 of FIG. 3 as explained above. For example, the electronic computing device monitors the communication between the dispatcher and the caller during the call (similar to block 305) and determines the type of call based on one or more of the monitored communication and metadata received via the input device (similar to block 310). The electronic computing device also determines the conversational procedure based on the type of call (similar to block 315) and compares a characteristic of the monitored communication to a constraint of the conversational procedure (similar to block 320).

In addition to this functionality that is similar to the method 300, at block 405, the electronic computing device determines a stress level in the voice of the caller. For example, the natural language processing engine may analyze at least one of a pitch, a frequency, and a volume of the voice of the caller to determine the stress level of the caller. As an example, when the caller is determined to be breathing heavily and is speaking at a high volume, the electronic computing device may determine that the caller has a high stress level. As another example, when the caller is determined to be speaking at a volume consistent with normal telephone conversation and is speaking at a speed consistent with normal human conversation, the electronic computing device may determine that the caller has a low stress level.

Using at least some of the above-noted information relating to the call, at block 405, the electronic computing device determines the severity level of the call. In some embodiments, the electronic computing device determines the severity level by generating an average or a weighted average of scores associated with each piece of the above-noted information. For example, the electronic computing device may generate a score on a scale of, for example, one to ten that indicates the severity level of the call based on each piece of the above-noted information.

For example, different types of calls may be determined to have different severity level scores. As an example, when the call relates to a cat stuck in a tree, the electronic computing device may determine that a severity level score for the incident type is one. However, when the call relates to a person having a heart attack, the electronic computing device may determine that a severity level score for the incident type is eight.

Similarly, different comparisons of the characteristic of the monitored communication to the constraint of the conversational procedure (as explained above in the method 300) may be determined to have different severity level scores. For example, when the comparison indicates that the dispatcher is following the conversational procedure and is proceeding through the conversational procedure at a speed that is faster than the expected amount of time to articulate predetermined content, the electronic computing device may determine that a severity level score for the comparison is two. On the other hand, when the comparison indicates that the dispatcher is deviating from the conversational procedure and is proceeding through the conversational procedure at a speed that is slower than the expected amount of time to articulate predetermined content, the electronic computing device may determine that a severity level score for the comparison is nine. In some embodiments, the electronic computing device may adjust the severity level score for the comparison based on the length of the conversational procedure. For example, when the conversational procedure is long and involves tasks that are expected to take multiple minutes, the electronic computing device may increase the severity level score for the comparison by, for example, two points.

Similarly, different stress levels of the voice of the caller may be determined to have different severity level scores. For example, when the caller is determined to have a high stress level, the electronic computing device may determine that a severity level score for the voice of the caller is eight. However, when the caller is determined to have a low stress level, the electronic computing device may determine that a severity level score for the voice of the caller is three.

In some embodiments, the electronic computing device may take an average or a weighted average of the severity level scores for each of the above-noted pieces of information explained above to determine a severity level of the call (for example, on a scale of one to ten). In some embodiments, additional information may also be used to determine the severity level of the call (for example, estimated time arrival of a first responder near the location of the incident, stress level in the voice of the dispatcher, and the like). In some embodiments, the severity level of the call is dynamic and changes during the call. In other words, the electronic computing device may continue to monitor the communication between the dispatcher and the caller to determine whether the type of call has changed, whether the dispatcher is following the conversational procedure in a timely manner, and whether the stress level of the voice of the caller has changed. When any of this information changes, the electronic computing device may update the proper severity level score(s) and determine an updated severity level of the call.

At block 410, the electronic computing device compares the severity level of the call with a predetermined severity level threshold. For example, the electronic computing device compares the average of the severity level scores described above to a predetermined severity level threshold (for example, six out of ten). When the severity level of the call is less than the severity level threshold, the method 400 repeats blocks 405 and 410 to dynamically determine the severity level of the call as explained above.

At block 415, the electronic computing device determines that the severity level of the call exceeds the predetermined severity level threshold. Continuing the example above, in such a situation, the electronic computing device has determined that the average of the severity level scores described above is greater than or equal to six. In some embodiments, the electronic computing device may determine to take action (at block 420) when one of the severity level scores of the above-noted pieces of information is very high (for example, nine or ten) even though the overall severity level of the call (in other words, the average of the severity level scores) is below the predetermined severity level threshold.

At block 420, the electronic computing device takes an action in response to determining that the severity level of the call exceeds the predetermined severity level threshold. The action taken by the electronic computing device may be similar to the example actions explained above with respect to block 330 of FIG. 3.

As an example implementation of the method 400, the caller may be calling to request instructions on how to handle a non-fatal bleeding wound. Based on a low stress level of the voice of the caller and the dispatcher accurately and timely proceeding through the first tasks of the conversational procedure corresponding to how to handle a non-fatal bleeding wound, the electronic computing device may determine not to take action to assist the dispatcher. However, in continuing to monitor the call, the electronic computing device may determine that the caller was unable to get the wound to stop bleeding within an expected amount of time in accordance with the conversational procedure. In such a situation, the electronic computing device may determine that the severity level of the call has increased above the predetermined severity level threshold and may take action in response to the severity level increase. For example, the electronic computing device may transmit information gathered from the monitored communication between the dispatcher and the caller to a communication device 200 of a first responder in response to determining that the severity level of the call exceeds the predetermined severity level threshold. As one example, the electronic computing device may dispatch the first responder to the location of the caller to aid the caller with the bleeding wound.

As another example implementation of the method 400, the caller may be a mother whose child is not breathing. The electronic computing device may determine that this type of incident is potentially fatal and that the stress level of the voice of the caller is very high. Accordingly, the electronic computing device may determine that the severity level of the call is very high (for example, nine or ten) and exceeds the predetermined severity level threshold. In response to this determination, the electronic computing device may dispatch a first responder to the location of the caller as soon as the location of the caller is determined. While the electronic computing device is communicating information to a communication device 200 of the first responder, the dispatcher may simultaneously be communicating with the caller to convey, for example, the steps to perform cardiopulmonary resuscitation. In this example, the electronic computing device determines the severity level of the call (at block 405) and takes action (at block 420) without evaluating compliance of communication of the dispatcher.

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (for example, comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. An electronic computing device comprising:
an input device;
a transceiver; and
one or more electronic processors communicatively coupled to the transceiver, the one or more electronic processors configured to
monitor communication between a dispatcher and a caller during a call,
determine a type of call based on one or more of the monitored communication and metadata received via the input device,
determine a conversational procedure based on the type of call,
compare a characteristic of the monitored communication to a constraint of the conversational procedure,
determine that the characteristic of the monitored communication is outside the constraint of the conversational procedure, and
take an action as a function of determining that the characteristic of the monitored communication is outside the constraint of the conversational procedure.

2. The electronic computing device of claim 1, wherein the one or more electronic processors are further configured to
determine a severity level of the call based on at least one of the group consisting of the type of call, a comparison of the characteristic of the monitored communication to the constraint of the conversational procedure, and a stress level of a voice of the caller;

compare the severity level of the call with a predetermined severity level threshold;

determine that the severity level of the call exceeds the predetermined severity level threshold; and transmit, via the transceiver, information gathered from the monitored communication to a communication device of a first responder in response to determining that the severity level of the call exceeds the predetermined severity level threshold.

3. The electronic computing device of claim 2, wherein the information gathered from the monitored communication includes at least one of the group consisting of a name of the caller, a location of the caller, a recommended route to the location of the caller, a health status of the caller, a health status of a victim, and a type of incident.

4. The electronic computing device of claim 1, wherein the characteristic of the monitored communication includes content of the monitored communication as articulated by the dispatcher, and the constraint of the conversational procedure includes a list and order of content that is to be articulated by the dispatcher.

5. The electronic computing device of claim 4, wherein the characteristic of the monitored communication further includes an amount of time that has elapsed since the beginning of the call, and the constraint of the conversational procedure further includes an expected amount of time for the dispatcher to articulate predetermined content of the conversational procedure.

6. The electronic computing device of claim 5, wherein the one or more electronic processors are configured to determine the expected amount of time for the dispatcher to articulate the predetermined content of the conversational procedure by determining a length of the list and an estimated amount of time to complete each task on the list.

7. The electronic computing device of claim 1, wherein the action is at least one of the group consisting of:

transmitting, via the transceiver, information gathered from the monitored communication to a communication device of a first responder as a function of determining that the characteristic of the monitored communication is outside the constraint of the conversational procedure; and switching the call to a communication device of a second dispatcher as a function of determining that the characteristic of the monitored communication is outside the constraint of the conversational procedure.

8. The electronic computing device of claim 7, wherein the one or more electronic processors are further configured to provide a notification to an output device of a communication device of the dispatcher that indicates that the information gathered from the monitored communication has been transmitted to the communication device of the first responder.

9. The electronic computing device of claim 1, wherein the one or more electronic processors are further configured to provide the conversation procedure to an output device of a communication device of the dispatcher.

10. A method of evaluating compliance of communication of a dispatcher, the method comprising:

monitoring, with an electronic computing device, communication between the dispatcher and a caller during a call;

determining, with the electronic computing device, a type of call based on one or more of the monitored communication and metadata received via an input device;

determining, with the electronic computing device, a conversational procedure based on the type of call;

comparing, with the electronic computing device, a characteristic of the monitored communication to a constraint of the conversational procedure;

determining, with the electronic computing device, that the characteristic of the monitored communication is outside the constraint of the conversational procedure; and taking an action, with the electronic computing device, as a function of determining that the characteristic of the monitored communication is outside the constraint of the conversational procedure.

11. The method of claim 10, further comprising:

determining, with the electronic computing device, a severity level of the call based on at least one of the group consisting of the type of call, a comparison of the characteristic of the monitored communication to the constraint of the conversational procedure, and a stress level of a voice of the caller;

comparing, with the electronic computing device, the severity level of the call with a predetermined severity level threshold;

determining, with the electronic computing device, that the severity level of the call exceeds the predetermined severity level threshold; and transmitting, via a transceiver, information gathered from the monitored communication to a communication device of a first responder in response to determining that the severity level of the call exceeds the predetermined severity level threshold.

12. The method of claim 11, wherein transmitting the information gathered from the monitored communication to the communication device of the first responder includes transmitting information that includes at least one of the group consisting of a name of the caller, a location of the caller, a recommended route to the location of the caller, a health status of the caller, a health status of a victim, and a type of incident.

13. The method of claim 10, wherein comparing the characteristic of the monitored communication to the constraint of the conversational procedure includes comparing content of the monitored communication as articulated by the dispatcher to a list and order of content that is to be articulated by the dispatcher.

14. The method of claim 13, wherein comparing the characteristic of the monitored communication to the constraint of the conversational procedure further includes comparing an amount of time that has elapsed since the beginning of the call to an expected amount of time for the dispatcher to articulate predetermined content of the conversational procedure.

15. The method of claim 14, further comprising determining the expected amount of time for the dispatcher to articulate the predetermined content of the conversational procedure by determining a length of the list and an estimated amount of time to complete each task on the list.

16. The method of claim 10, wherein taking the action includes at least one of the group consisting of:

transmitting, via a transceiver, information gathered from the monitored communication to a communication device of a first responder as a function of determining that the characteristic of the monitored communication is outside the constraint of the conversational procedure; and switching the call to a communication device of a second dispatcher as a function of determining that the characteristic of the monitored communication is outside the constraint of the conversational procedure.

17. The method of claim 16, further comprising providing a notification to an output device of a communication device of the dispatcher that indicates that the information gathered from the monitored communication has been transmitted to the communication device of the first responder.

18. The method of claim 10, further comprising providing the conversational procedure to an output device of a communication device of the dispatcher.

\* \* \* \* \*